United States Patent [19]

Smith

[11] Patent Number: 5,050,690

[45] Date of Patent: Sep. 24, 1991

[54] IN-SITU STRESS MEASUREMENT METHOD AND DEVICE

[75] Inventor: John C. Smith, Pasadena, Calif.

[73] Assignee: Union Oil Company of California, Los Angeles, Calif.

[21] Appl. No.: 510,480

[22] Filed: Apr. 18, 1990

[51] Int. Cl.$^5$ .................... E21B 49/00; G01B 5/30; G01N 3/10

[52] U.S. Cl. .................... 175/50; 175/230; 166/250; 73/151; 73/783; 73/784

[58] Field of Search .................... 175/40, 50, 230; 166/250, 101, 188; 73/151, 783, 784, 799; 299/21

[56] References Cited

U.S. PATENT DOCUMENTS

| | | | |
|---|---|---|---|
| 2,946,565 | 7/1960 | Williams | 175/230 |
| 2,957,341 | 10/1960 | Menard | 73/784 |
| 3,107,729 | 10/1963 | Barry et al. | 175/40 |
| 3,606,924 | 9/1971 | Malone | 175/230 |
| 3,796,091 | 3/1974 | Serata | 73/784 |
| 3,858,441 | 1/1975 | Comeau | 73/784 |
| 4,030,345 | 6/1977 | Edmond et al. | 73/784 |
| 4,372,380 | 2/1983 | Smith et al. | 166/250 |
| 4,491,022 | 1/1985 | de la Cruz | 73/783 |
| 4,598,591 | 7/1986 | Baud | 73/784 |
| 4,665,984 | 5/1987 | Hayashi et al. | 166/250 |
| 4,711,501 | 12/1987 | Maeda et al. | 299/21 |
| 4,733,567 | 3/1988 | Serata | 73/784 |
| 4,899,320 | 2/1990 | Hearn et al. | 73/151 |

OTHER PUBLICATIONS

"The Hydrofacturing Stress Measuring Method and Recent Field Results" by B. C. Haimson, Int. J. Rock Mech. Min. Sci & Geomech. Abst., vol. 15, pp. 167–178, 1978.

"Earth Stress Measurements in the South Belridge Oil Field, Kern County, Calif.," by K. S. Hansen and W. R. Purcell, 1986, SPE #15641.

"Production Operations", vol. 1, by T. O. Allen and A. P. Roberts, Retrievable Packers, pp. 172–180, 1982.

"Long, Cement Inflatable Formation Packers", Completion Tool Company, CTC, Austin, Texas, Payzone Literature.

"Fundamentals of Rock Mechanics", by J. C. Jaeger and N. G. W. Cook, Chapter 15, pp. 384–394, London.

"Issues in Rock Mechanics, Chapter 15, Status of the Hydraulic Fracturing Method for In-Situ Stress Measurements," by M. Zoback et al., pp. 143–156, 1982.

"The Interpretation of Hydraulic Fracturing Pressure-Time Data for In-Situ Stress Determination," by S. H. Hickman et al., pp. 44–54, of Hydraulic Fracturing Stress Measurements, National Academy Press, 1983.

Primary Examiner—Bruce M. Kisliuk
Attorney, Agent, or Firm—Gregory F. Wirzbicki; William O. Jacobson

[57] ABSTRACT

A method for obtaining in-situ stress measurements in a well is accomplished by installing a membrane packer on a drill string. The packer membrane is attached near the drilling tool and is capable of being radially expanded by fluid pressure to abut against the borehole. When a measurement of the in-situ stress is desired, a 3 way valve is actuated to divert drill string fluid into the packer until the membrane contacts the borehole. Further increments of fluid addition at this point are accomplished only by large increases in inflation fluid pressure. Pressure is increased (with little increase in volume) at a ramp rate until it reaches a value equal to the least principal stress, at which point the formation microfractures. The microfracture(s) result in a decreased pressure and/or volume ramp rate, which indicate their presence. Further pressurization would generate similar indications of fractures resulting from intermediate and maximum principle stresses. After fracturing, the pressure is reduced, and the 3 way valve is actuated to return the fluid to the drill bit.

15 Claims, 2 Drawing Sheets

IN-SITU STRESS MEASUREMENT METHOD AND DEVICE

FIELD OF THE INVENTION

This invention generally relates to the drilling of subterranean formations. More specifically, the invention is concerned with providing a drilling means to economically and reliably determine a portion of the in-situ stresses within the formation.

BACKGROUND OF THE INVENTION

In drilling, producing or injecting hydrocarbons or other fluids within a subterranean formation, it is often necessary or desirable to determine the in-situ formation stresses. While drilling a borehole, in-situ stress can be used to determine the maximum mud weight (above which lost circulation or blow out risks are unacceptable), and the minimum mud weight to avoid the risk of borehole collapse. While completing a well, in-situ stress can form the basis for determining whether the borehole needs to be gravel packed and for engineering a hydraulic fracture treatment.

Two basic techniques for determining in-situ stress are known: 1) direct measurements of force and area; and 2) measurement of displacements induced by stress. Displacement measurements may be accomplished in conjunction with cuts to relieve in-situ stress. One cutting technique creates a slot in the borehole face formation, completely relieving the slot surfaces of the stresses across them. The relief results in expansion and/or displacement which can be measured. The slot surfaces can also be forced back into the undisturbed condition and the force (and stress if area is known) and strain can be measured. However special cutting tools are required, and creep, grouting and cancellation effects can introduce serious errors to the stress and strain determinations.

Force techniques apply stress to the surface of a borehole, producing deformations (strains) an fractures which can be used to determine the direction of the minor principal stress. A fluid pressure fracturing (hydrofracturing) technique obtains pressure data which can be used to determine some of the in-situ stress. Fluid flow and pressure is increased to a sealed off axial section of the borehole until fractures develop and propagate. The flow is reduced and the pressure is measured, called the instantaneous shut-in pressure (ISIP). Since the borehole at depth is typically under compressive load and the tensile strength capability of rock is generally small, the increasing hydraulic pressure relieves the compressive in-situ stress until tensile fracture occurs. Fracture is typically in a direction perpendicular to the least principal horizontal stress.

It is known that the ISIP after initial fracturing is related to the least principal stress. This phenomenon (shut in pressure at after initiation/opening of fracture determining the least principal stress) has been well-demonstrated by laboratory and theoretical studies. The methods of calculation are described in two references: 1) Zoback, M. D. and Haimson, B. C., "Chapter 15, Status of the Hydraulic Fracturing Method for In-Situ Stress Measurements" in: Goodman, R. E. and Heuze, F. E., Editors, "Issues in Rock Mechanics, Proceedings Twenty-Third Symposium on Rock Mechanics, The University of California, Berkeley, Calif., Aug. 25-27, 1982" (New York, Society of Mining Engineers of the American Institute of Mining, Metallurgical and Petroleum Engineers, Inc., 1982), pp 143-156; and 2) a paper by Hickman, S. H., and Zoback, M. D., entitled "The Interpretation of Hydraulic Fracturing Pressure-Time Data for In-Situ Stress Determination" in: U.S. Geological Survey, "Hydraulic Fracturing Stress Measurements" (Washington, National Academy Press, 1983), pg 44-54, said chapter and paper being incorporated hereinto by reference.

The instantaneous shut-in pressure (direct injection of fluid is halted and pressure measured) rather than breakdown pressure (fluid pressure measured when fracture occurs) has been used in these incorporated references to determine in-situ stresses because of several factors. Theoretical factors avoided by using ISIP include accounting for injection pressure loss or frictional flow of fluids into the formation or fractures, potential fracture propagation away from the borehole, and the presence of pre-existing fractures at the borehole. Since the hydraulic fluid flow cannot be shut in instantaneously and the presence of other factors is generally unknown, the ISIP measurements after fracture initiation may no longer be suitable for determining the least principal stress near the borehole. In addition to these theoretical and practical problems is determining in-situ stresses, shut-in pressure may be indistinct (e.g., pressure may rapidly decrease to zero when injecting fluid flow is stopped).

These references and others have attempted to correct for these factors/problems in measuring ISIP and determining in-situ stress. Correction methods include multiple injection flows and repeated measurements of shut-in pressures, pressure decrease rate analysis, pressure increase/build up upon re-pressurization analysis, and fracture re-opening pressurization analysis. In addition, a separate determination of fracture magnitude and direction may be required.

All of the current in-situ stress measurements methods require special downhole tools or fluid injection and procedures. If the in-situ stress determinations are required during a drilling operation (including completion, logging and related activities), the drilling operations must be interrupted, operational equipment removed, special equipment installed, pressure, force, and/or displacement data obtained, in-situ stress calculated, the special equipment removed, and operational equipment replaced.

None of the current or alternative approaches known to the inventor eliminates the special equipment installation, removal, and interruption problems in order to obtain in-situ stress measurements. Drilling interruption may also cause additional problems, such as thermal soak or shock, cave in, settling, and stuck pipe.

SUMMARY OF THE INVENTION

The present invention achieves a more convenient method for obtaining some in-situ stress measurements by installing a flow diverter valve and a membrane packer-like device just above the bottom hole assembly (including a drill bit) on a drill string. The packer membrane is capable of being radially expanded by fluid pressure to contact the borehole. When determination of the in-situ stress at a zone of interest is desired, the flow diverter valve is actuated to divert drill string fluid into the packer until the membrane contacts the borehole within the zone of interest.

Further increments of fluid addition are now accomplished only by large increases in inflation fluid pressure. Pressure is increased (with little increase in volume) at a rapid rate until it reaches a value based upon the least principal stress near the well bore, at which point the formation at the borehole begins to fracture (i.e., microfracture) in a plane perpendicular to the least principal horizontal stress, and the pressurization rate changes (delta pressure/delta volume).

Because of the membrane, no loss of fluid/frictional pressure drop factors are present. Because the pressure data are not taken after the fluid flow stops, the pressure data at the point of fracture can be theoretically equivalent to ISIP during hydrofracturing operations. The microfracture(s) do cause a change in the rate of pressurization which can be measured. The measured inflection point on a pressure-time slot is comparable to the instantaneous shut-in pressure measurements. Further pressurization can be used to confirm data or can generate similar indications of fractures resulting from intermediate and maximum principle stresses.

After fracturing and determining the in-situ stresses of interest, the fluid pressure within the membrane is reduced. Pressure can be reduced by surface pump controls or by actuating the diverter valve to return the fluid flow from the membrane to the drill bit.

By providing a known volume of pressurized fluid to the membrane, the bearing stresses and strains can be controlled. Like the current two packer isolation and hydrofracturing techniques, the present invention also produces a fluid pressure radially bearing on the borehole, but it avoids the need for removal of drilling equipment, providing a special string, two packers, direct application of pressure and measurement of fracture direction and magnitude. It also allows repeated pressurization to verify/correct data and post-drilling inspection of the membrane to determine fracture direction. By calculations based on fluid pressure, pressure rate of increase, pressure rate inflection point(s) and membrane volume changes, some of the in-situ stresses are calculated without the separate equipment or major drilling interruption. The present invention is also safe and cost effective.

BRIEF DESCRIPTION OF THE DRAWINGS

In these Figures, it is to be understood that like reference numerals refer to like elements or features.

DETAILED DESCRIPTION OF THE INVENTION

Figure 1A:
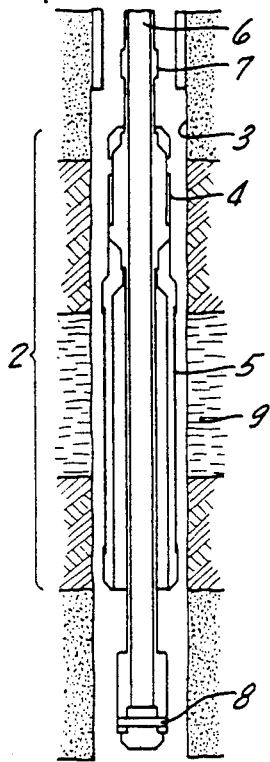
FIG. 1a-1d show schematic cross-sectional views of a prior art open hole packer.

FIG. 1 shows a sequence of schematic crosssectional views of a prior art open hole inflatable packer 2 sealing off a section of borehole 3. FIG. 1a shows the packer 2 after being run into borehole 3. The packer 2 consists of a fill, check valve and vent assembly 4, and a membrane 5 filled by conducted fluid 6 from within tubing or drill string 7. At the end of the drill string 7 is a shear plug 8. The drill string 7 is lowered into the hole until the packer 2 is proximate to the portion of formation 9 desired to be sealed or isolated.

Figure 1B:
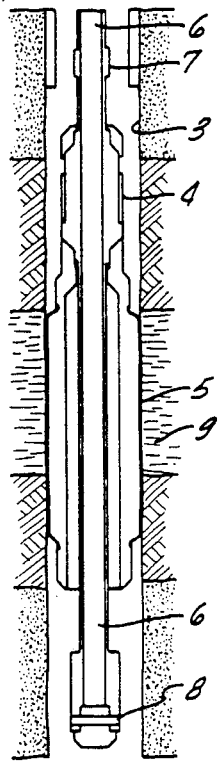

FIG. 1b shows the membrane 5 inflated by the conducted fluid 6. The inflated membrane is n contact with the borehole 3 wall portion or face of formation 9 to be sealed off. The fluid 6 must pass through assembly 4 which includes a check valve, while the remainder of conducted fluid 6 is prevented from escaping to the borehole by shear plug 8. The fluid pressure is increased until the membrane is firmly set against the formation 9, sealing the borehole at this location.

Figure 1C:
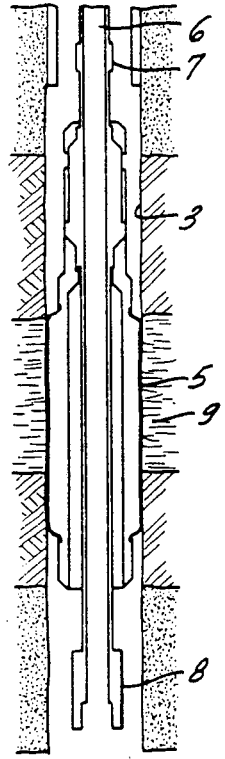

Once the membrane 5 is fully inflated and set, the shear plug 8 can be ruptured as shown in FIG. 1c. The check valve of assembly 8 maintains the inflating and setting of the sealing packer 2, preventing the inflating fluid within the membrane 5 from discharging to the borehole 3. Rupture of the shear plug 8 may be accomplished by a bar being dropped or a rupture pressure being applied.

Figure 1D:
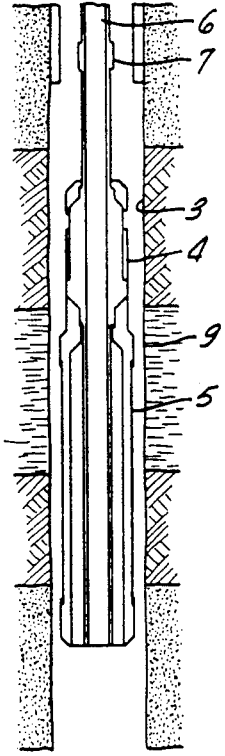

When packer deflation is desired, membrane fluid is be discharged through vents in assembly 4. FIG. 1d shows the membrane deflated after the vents in the assembly 4 have been opened. Vent opening may be accomplished remotely, such as by drill string rotation, axial motion, or a separate pressure actuator.

Figure 2:
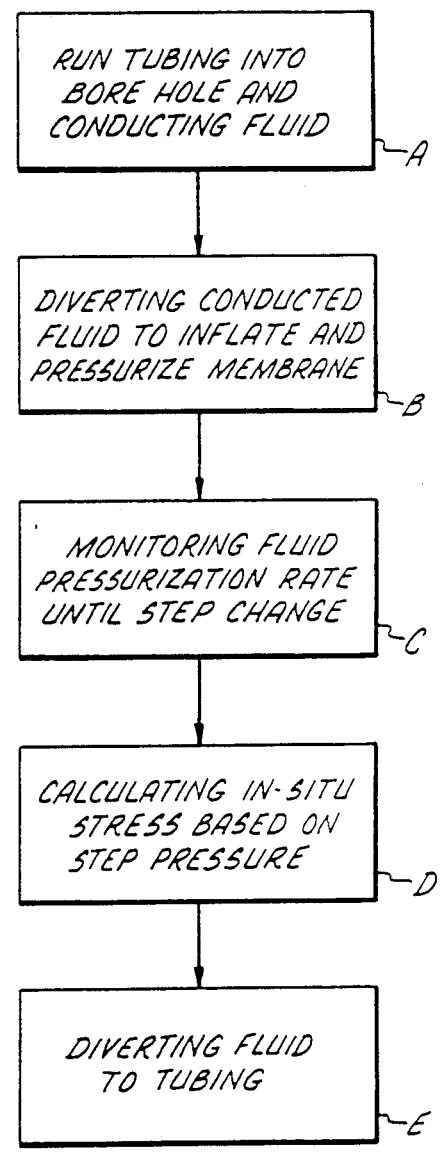
FIG. 2 shows a process flow chart of measuring in-situ stress.

The simplest embodiment of the present invention method uses the prior art open-hole packer (as shown in FIG. 1) attached to tubing, run into the borehole, and inflated. However, as shown in FIG. 2, the method goes beyond the prior art steps by using a packer which can microfracture the formation, attaching the packer to a drilling string having a drilling tool or other operating fluid handling device attached at one end and obtaining fluid pressure data (as shown in FIG. 2, step C) until microfracture(s) occur. Using these data, in-situ stress(es) are calculated (FIG. 2, step D) using methods similar to ISIP methods previously discussed.

The drill string having a packer assembly attached is run down the borehole and fluid is conducted within the tubing in FIG. 2, step A. The conducted fluid is typically a drilling mud supplied from a surface pump, rather than a fracture fluid. The inflatable packer may be a CTC PAYZONE model, but other open hole inflatable packers can also be used.

FIG. 2, step B, diverts the conducted fluid from the tubing into the interior of the membrane. The diverting means may be a pressure actuated three way valve or separate fill and vent/drain valves. The diverted fluid first inflates the membrane until it contacts the borehole as shown in FIG. 1b.

FIG. 2, step C, obtains fluid property data during pressurization of the membrane after inflation to the walls of the borehole and formation face. The increasing pressure deforms the borehole surface until a fracture occurs. This is detected by a step change in the rate of volume and/or pressure increase, e.g., an inflection point in the pressure-time data. Pressure and/or volume step changes in rates can be detected at the surface and downhole fluid conditions can be determined f om surface measurements.

Pressure rates prior to microfracture can range from 1 MPa/sec or less, which tend to produce few fractures, to between 1 MPa/sec and $10^7$ MPa/sec, which tend to produce multiple fractures. Volume inflow rates would be dependent upon the pressurization rates and formation deformation. Detection of the rate change(s) can be accomplished with current technology pressure, flow and other fluid property detectors. Fluid property data can be corrected to calculated downhole conditions using known depth, fluid density, and other parameters.

FIG. 2, step D, uses the pressure and volume data to calculate in-situ stress. At least one of the in-situ stresses can be calculated from aforementioned incorporated references. Other in-situ stresses may be determined from multiple applications of pressure to the membrane and other data.

FIG. 2, step E, rediverts the inflating fluid back to the drilling bit. This can be accomplished by a three way valve de-actuated by a set differential pressure. The actuating differential pressure is higher than a set differential for normal drilling operations. Actuation pressure differential diverts fluid to the membrane and reduction re-diverts the fluid flow to the drilling operation. Other remote actuation means are also possible.

Figure 3A:
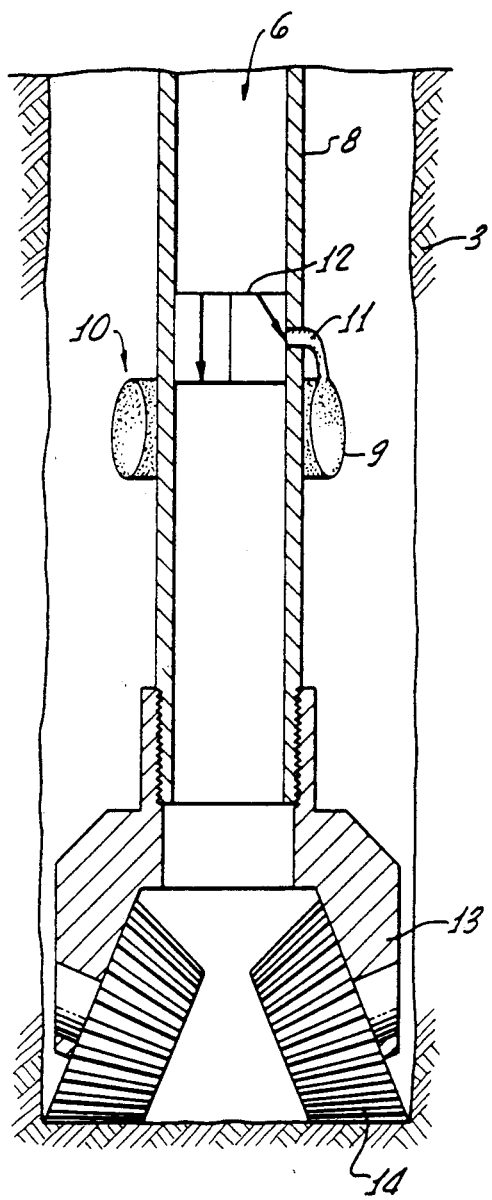
FIGS. 3a and 3b show front views of an alternative drilling tool embodiment.
Figure 3B:
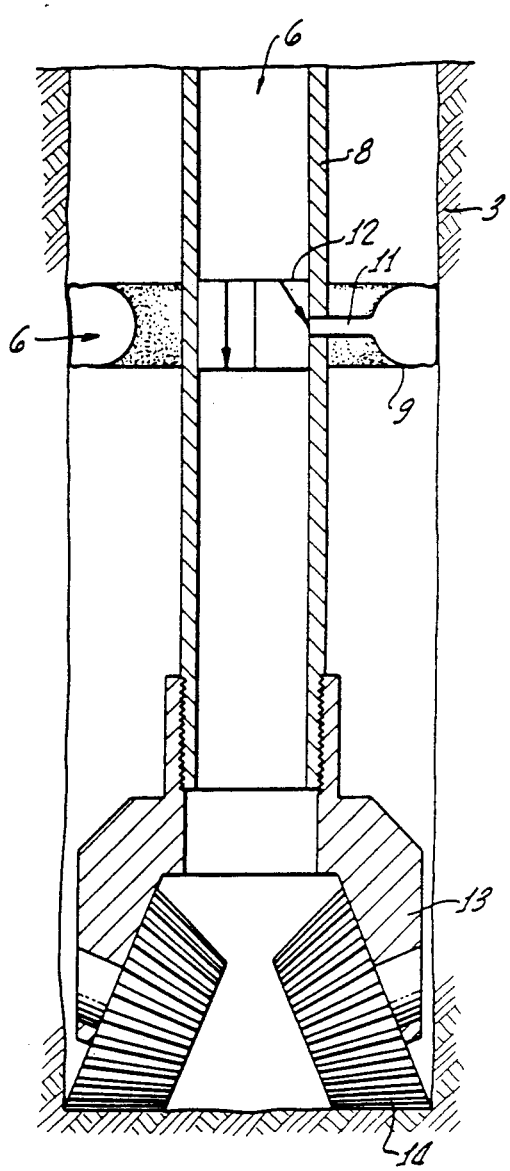

FIG. 3 shows two cross-sectional schematic views of an alternative embodiment. Alternative membrane 9 is inner-tube-shaped to allow fluid passage in the annular space 10 between the drill string 8 and borehole 3. Fluid passage is possible when the membrane 9 is deflated as shown in FIG. 3a) or inflated (as shown in FIG. 3b). The alternative membrane 9 is inflated through inflation port and stem 11. Fluid flow through inflation port 11 is controlled by a three way valve 12. The three way valve restricts, but does not stop fluid passage to a drilling tool 13 when actuated to inflate and pressurize the alternative membrane 9.

The process of using the alternative in-situ stress measurement device (shown in FIGS. 3a and 3b) during drilling involves supplying fluid 6, such as drilling muds, to the drilling tool 13. The pressure and flow of drilling muds flowing down the drill string 8 rotate drill bits 14 and carry cuttings up the annulus 10 for removal at the surface. When pressure and volume data (i.e., in-situ stress measurements) are desired, the three way valve 12 is actuated by increased fluid pressure (or other means) and at least a portion of the drilling mud flow is diverted to the port 11 and alternative membrane 9. The actuation restricts mud flow, maintaining circulation for resumption of drilling. If the actuation and pressurization is quick enough (e.g., little translation of drill string) and sufficient fluid flow is available, drilling does not even have to be interrupted at all. However, if required, the three way valve may also divert all fluid to the alternative membrane.

After actuation, the membrane radially expands and inflates with fluid, contacting the walls of the borehole but not filling the annulus between the drill string 8 and borehole 3 as shown in FIG. 3b. In order to ensure fluid passage past the alternative membrane in the annulus 10 after inflation, hinged struts or other ported structural stand-offs from the drill string to the inner diameter of the inflated membrane may also be provided.

Once the membrane is set against the borehole wall, further increases in pressure and flow into the membrane can be measured to determine a formation modulus and in-situ stress from calculations in the incorporated chapter or paper references. Set conditions can be determined from the surface by fill times or a lack of further fluid flow into the alternative membrane at a set pressure if all fluid is diverted to the alternative membrane. If a portion of the flow continues to the drill bit, the stabilization of fluid flow at this restricted flow rate is used to determine setting of the alternative membrane.

Increasing drilling mud pressure is applied from surface mud pumps, the pressures and flow rates measured, and alternative membrane pressure and flow calculated from surface measurements. Microfractures will cause an abrupt change in pressure and volume rates of increase. When this is detected, the calculated membrane pressure (less any change in pressure across the alternative membrane) forms the basis for determining the minimum principal in-situ stress as shown in the incorporated chapter and paper references. Further increases in pressure can be accomplished if added in-situ stress measurements are needed.

When satisfactory data is obtained, fluid pressures can be reduced, deflating the membrane and returning it to the shape shown in FIG. 3a. In conjunction with deflation, the three way valve 12 is actuated to redirect all or the diverted portion of the fluid from the surface mud pumps (not shown for clarity) to the drilling tool 13. Deflation may also be accomplished by a differential pressure relief valve after rediverting the flow, as well as the direct flow through port 11.

The method of the invention allows in-situ stress determinations during all phases of drilling a well, including completion, logging, production, steam injection, start-up, shutdown, storage, maintenance, and inspection. Liquid, nearly incompressible inflation fluids with controlled density, such as drilling muds, are the preferred conducted fluids, but compressible gases may also be used.

The membrane component varies depending upon the size of the borehole and drill string used, as well as the design fluid pressure, need for circulation during inflation and deflated fluid flow rates through the annulus. The three-way valve may also include flow limitation, back pressure control, and relief devices.

Still other alternative embodiments are possible. These include: a plurality of membranes to obtain data on multiple formation zones at the same time (generating multiple inflection point data for determining different in-situ stresses), extending or limiting the contact area of the membrane and controlling the stiffness of the membrane (minimizing tangential loads and fracture propagation), attaching the membrane to the drilling tool instead of the drill string (forming a single drilling tool and in-situ stress measuring device), further separating the membrane from the drill bits (to minimize the possibility of membrane damage from drilling operation), having a membrane composed of rigid panels joined with flexible materials (making the membrane more rugged), having the alternative struts composed of porous material (allowing fluid circulation when membrane is inflated), having the struts slidably hinged to the duct (to set apart a portion of the membrane from the drill string when membrane is inflated and drill string is moving), a check valve in the drill string upstream of the plenum (preventing back flow of fluids during deflation), detecting formation fracturing using temperature or other fluid property data during pressurization, an having the deflated and/or inflated membrane located in a protective enclosure(s).

While the preferred embodiment of the invention has been shown and described, and some alternative embodiments also shown and/or described, changes and modifications may be made thereto without departing from the invention. Accordingly, it is intended to embrace within the invention all such changes, modifications and alternative embodiments as fall within the spirit and scope of the appended claims.

What is claimed is:

1. A method for determining an in-situ stress of a subterranean formation portion penetrated by a borehole containing a drill bit attached to a fluid conducting drill string, the method using: a source of pressurized fluid; a membrane attached to the drill string and inflatable by the fluid, wherein the membrane is capable of causing the formation to fracture when inflated; and a means for diverting at least a portion of the fluid from the drill string to the membrane, said method comprising:
- a. running the drill string into the borehole, until the membrane is located proximate to the portion of the formation;
- b. diverting at least a portion of the fluid from the drill string to within the membrane causing the membrane to tend to inflate;
- c. inflating the membrane until the membrane contacts the formation portion;
- d. increasing the pressure of the fluid within the membrane while measuring the rate of pressure change until a rate change caused by a formation fracture is detected; and
- e. calculating an in-situ stress based upon the pressure at which the rate change occurred.

2. The method of claim 1 which also comprises:
- f. reducing the fluid pressure; and
- g. rediverting all of the conducted fluid to the drill bit assembly.

3. A method for determining an in-situ stress of a material at a location under a compressive stress penetrated by a walled cavity, the method using: a cavity insertable duct for conducting fluid, said cavity and duct forming an annular space between said duct and said cavity wall; a fluid handling device attached at an insertable end of said duct; and a fluid inflatable membrane attached to the duct, said inflated membrane capable of exerting a formation fracturing pressure within said annulus, said method comprising the steps of:
- a. inserting said duct into said cavity until said membrane is located proximate to said location;
- b. supplying pressurized fluid to said duct;
- c. diverting at least a portion of said fluid from said duct to said membrane causing inflation;
- d. inflating the membrane within the annular space until the membrane contacts a portion of the cavity wall at an inflation volume;
- e. increasing the inflation pressure and volume of said fluid within said membrane while measuring a fluid property until a change caused by formation fracturing is detected; and
- f. calculating an in-situ stress based upon the measured pressure at which said rate step change occurs, wherein said calculating is in the absence of data from a radial displacement transducer proximate to said location.

4. The method of claim 3 which also comprises:
- g. reducing the pressure within said membrane; and
- h. returning the diverted fluid to said insertable end through a passage.

5. A method for determining an in-situ stress of a material at a location under a compressive stress penetrated by a walled cavity, the method using: a cavity insertable duct for conducting fluid, said cavity and duct forming an annular space between said duct and said cavity wall; a fluid handling device attached at an insertable end of said duct; and a fluid inflatable membrane attached to the duct, said inflated membrane capable of exerting a formation fracturing pressure within said annulus, said method comprising the steps of:
- a. inserting said duct into said cavity until said membrane is located proximate to said location;
- b. supplying pressurized fluid to said duct wherein said fluid handling device continues to operate using a portion of the conducted fluid when said fluid portion is diverted;
- c. diverting at least a portion of said fluid from said duct to said membrane causing inflation;
- d. inflating the membrane within the annular space until the membrane contacts a portion of the cavity wall at an inflation volume;
- e. increasing the inflation pressure and volume of said fluid within said membrane while measuring a fluid property until a change caused by formation fracturing is detected; and
- f. calculating an in-situ stress based upon the measured pressure at which said rate step change occurs.

6. The method of claim 5 wherein said membrane is shaped and dimensioned to avoid filling said annular space and allow fluid flow within said annular space when said membrane is inflated.

7. The method of claim 6 wherein at least a portion of said membrane is set apart from said duct when said membrane is inflated.

8. A fracture producing apparatus for measuring an in-situ stress in a substrate formation penetrated by a borehole, said apparatus comprising:
- borehole insertable tubing for conducting a fluid to and out of a first insertable end, said inserted tubing and said borehole forming an annular space;
- a fluid port located apart from said first end, capable of transmitting fluid from the interior of said tubing to the exterior of said tubing;
- a fluid inflatable plenum for containing said transmitted fluid, said plenum attached to said fluid port and located within said annular space, wherein said plenum is capable of exerting a generally radial formation fracturing pressure within said borehole;
- means for restricting the flow of fluid conducted to said first insertable end, said restricting means located between said first end and said fluid port, wherein said restricting means diverts at least a portion of said fluid from said tubing to said plenum;
- means for measuring a fluid property within said plenum when said formation fractures; and
- means for calculating said in-situ stress based upon said measured fluid property, wherein said calculating is in the absence of a radial displacement measurement proximate to said subsurface formation.

9. A fracture producing apparatus for measuring in-situ stress within a borehole extending from a surface and penetrating a subsurface formation comprising:
- tubing for conducting a fluid, extending from the surface into said borehole, forming an annular-like space between said tubing and said borehole;
- an operating device attached to one end of said tubing and locatable within said borehole;
- an inflatable plenum for containing said fluid, said plenum attached to said tubing near said operating device and capable of fracturing said formation when inflated by said fluid;
- means for inflating said plenum within said annular-like space until formation fracture;
- means for measuring a property of the inflating fluid when said formation fractures, wherein said property is related to an in-situ stress of the formation prior to inflating;
- means for calculating said in-situ stress based upon said inflating fluid property, wherein said calculating excludes a measured radial displacement proximate to said subsurface formation; and means for deflating said plenum.

10. The apparatus of claim 9 which also comprises first means for preventing backflow of said pressurized fluid towards said surface within said tubing.

11. The apparatus of claim 10 wherein said means for inflating is a fluid passage and which also comprises a remotely controlled valve capable of restricting said fluid within said fluid passage.

12. The apparatus of claim 11 which also comprises means for spacing apart said tubing and said inflated plenum so as to allow fluid to flow in said annular-like space.

13. A fracture producing apparatus for measuring an in-situ stress in a material penetrated by a cavity, said apparatus comprising:
cavity insertable duct for conducting a pressurized fluid to and out of a first insertable end;
fluid port located apart from said first end, capable of transmitting fluid from the interior of said duct to the exterior of said duct;
a fluid inflatable plenum attached to said fluid port for containing said transmitted fluid, wherein said plenum is capable of inflating radially outward and is also capable of exerting a material fracturing pressure when said plenum is inflated and is in contact with said material without rupturing;
means for restricting the flow of fluid conducted to said first insertable end, said restricting means located between said first insertable end and said fluid port, wherein said restricting means diverts at least a portion of said fluid from said duct to said plenum; and
means for measuring a fluid property within said plenum; and
means for calculating said in-situ stress based upon said measured fluid property, wherein said calculating is in the absence of a measured radial displacement proximate to said subsurface formation.

14. The apparatus of claim 13 wherein said duct extends from a source of said pressured fluid to said insertable end along a major axis, and wherein said inflating is in all radially outward directions from said axis, which apparatus also comprises:
means for spacing apart said duct from said inflated plenum so as to allow fluid from said insertable end to return to said fluid source outside of said duct; and
means for deflating said plenum.

15. A method for determining an in-situ stress of a material penetrated by a walled cavity, the method using: a cavity insertable duct for conducting fluid, said cavity and inserted duct forming an annular space between said duct and said cavity wall; a fluid handling device attached at an insertable end of said duct; and a fluid inflatable membrane attached to the duct, said inflated membrane capable of exerting a formation fracturing pressure within said annulus, said method comprising the steps of:
a. inserting said duct into said cavity;
b. supplying fluid to said duct wherein said fluid handling device accepts a first portion of the supplied fluid to said duct;
c. diverting a second portion of said supplied fluid from said duct to said membrane within the annular space;
d. while diverting, measuring a fluid property until a change caused by formation fracturing is detected; and
e. calculating an in-situ stress based upon the measured property at which said change occurs.

* * * * *